United States Patent
Dye et al.

[19]

[11] Patent Number: 6,120,546
[45] Date of Patent: *Sep. 19, 2000

[54] IMPLANTABLE PROSTHESIS HAVING SPRING-ENGAGED HOLE PLUGS

[75] Inventors: Donald Dye, Pflungerville; Gary Sederholm, Austin, both of Tex.

[73] Assignee: Sulzer Orthopedics Inc., Austin, Tex.

[*] Notice: This patent is subject to a terminal disclaimer.

[21] Appl. No.: 09/234,990

[22] Filed: Jan. 21, 1999

Related U.S. Application Data

[63] Continuation of application No. 08/985,533, Dec. 5, 1997, abandoned.

[51] Int. Cl.[7] .................................................. A61F 2/34
[52] U.S. Cl. .................................. 623/22.34; 623/18.11
[58] Field of Search ........................... 623/18.11, 20.15, 623/22.34, 22.35

[56] References Cited

U.S. PATENT DOCUMENTS

| | | |
|---|---|---|
| 4,563,778 | 1/1986 | Roche et al. . |
| 5,171,276 | 12/1992 | Caspari et al. . |
| 5,314,487 | 5/1994 | Schryver et al. . |
| 5,571,198 | 11/1996 | Drucker et al. . |
| 5,609,648 | 3/1997 | Oehy et al. . |
| 5,645,606 | 7/1997 | Oehy et al. . |
| 5,782,929 | 7/1998 | Sederholm ............................. 623/22 |
| 5,911,758 | 6/1999 | Oehy et al. ............................. 623/20 |
| 5,935,174 | 8/1999 | Dye ....................................... 623/22 |

*Primary Examiner*—Bruce Snow
*Attorney, Agent, or Firm*—Philip S. Lyren

[57] ABSTRACT

An implantable orthopedic prosthesis. A prosthetic component includes a wall having a first surface for engaging bone and a second surface. The wall defines a hole therethrough extending from the second surface to the first surface. A plug is removably disposed in the hole. The plug includes a peripheral rim spring-biased radially outwardly in frictional engagement with the sidewall of the hole. The plug is useful for occluding the hole to alleviate the risk of polyethylene wear particles migrating through an unused hole into contact with bone.

12 Claims, 2 Drawing Sheets

IMPLANTABLE PROSTHESIS HAVING SPRING-ENGAGED HOLE PLUGS

This application is a continuation of Ser. No. 08/985,533 filed Dec. 5, 1997, abandoned.

BACKGROUND OF THE INVENTION

1. Field of the Invention

The present invention relates generally to implantable prostheses for replacing human skeletal joints, and relates more particularly to a prosthetic component having one or more holes therethrough for receipt of a bone screw or instrument.

2. Background Information

Implantable orthopedic prostheses, in one form, comprise manufactured replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip joint and the knee joint are most often treated with such prostheses. The hip and knee joints are major weight bearing joints and degenerate more quickly than other joints in case of abnormality. Also, the hip and knee joints play a critical role in ambulation and quality of life, resulting in great demand for surgical correction of abnormalities.

The human hip joint involves two bones: the femur and the pelvis, each having a smooth articulation surface arranged for articulation against an adjacent articulation surface of the other bone. The femur includes at its proximal extremity a head having a convex, generally spherically contoured articulation surface. The pelvis, in pertinent part, includes an acetabulum having a concave, generally spherically contoured articulation surface. The mutually engaging articulation surfaces of the femur and the pelvis together form, functionally, a ball-and-socket joint.

One or both of the articulation surfaces of the hip joint may fail to act properly, requiring the defective natural articulation surface to be replaced with a prosthetic articulation surface provided by an implantable prosthesis. To fit defects of varying scope, while allowing healthy portions of the hip joint to be conserved, a range of types of orthopedic implants is available. The range extends from total hip prosthesis systems for replacing the articulation surfaces of both the femur and the pelvis, to simpler systems for replacing only the femoral articulation surface. Commonly employed orthopedic hip prostheses include components that fall within one of three principle categories: femoral stems, femoral heads and acetabular cups. A so-called "total" hip prosthesis includes components from each of these categories. The femoral stem replaces the proximal end of the femur and includes a distal stem received within the medullary canal at the proximal end of the femur. The femoral head replaces the natural head and articulating surface of the femur. The acetabular cup replaces the natural socket and articulating surface of the acetabulum of the pelvis. In some designs, the stem and head are an integral, unitary component, but more often the stem and head are separate modular components designed to be assembled to suit the anatomical needs of the patient. A so-called "bipolar" hip prosthesis includes only a femoral stem and a head component. The femoral part of the hip joint is replaced with a femoral stem supporting an artificial femoral head. The latter includes an inner head, fixed to the femoral stem, that articulates within an outer head. The outer head articulates directly against the natural acetabulum. Similarly, a so-called "unipolar" hip prosthesis also includes only a femoral stem and a head components. The femoral part of the hip joint is replaced with a femoral stem supporting an artificial femoral head. The femoral head articulates directly against the natural acetabulum while remaining fixed relative to the femoral stem.

The human knee joint involves three bones: the femur, the tibia and the patella, each having smooth articulation surfaces arranged for articulation on an adjacent articulation surface of at least one other bone. The femur includes at its distal extremity an articulation surface having medial and lateral convex condyles separated posteriorly by an intercondylar groove running generally in the anteriorposterior direction, the condyles joining at the distal-anterior face of the femur to form a patellar surface having a shallow vertical groove as an extension of the intercondylar groove. The patella includes on its posterior face an articulation surface having a vertical ridge separating medial and lateral facets, which facets articulate against the patellar surface of the femur and against the medial and lateral condyles during flexion of the knee joint, while the vertical ridge rides within the intercondylar groove to prevent lateral displacement of the patella during flexion. The tibia includes at its proximal end an articulation surface having medial and lateral meniscal condyles that articulate against the medial and lateral condyles, respectively, of the femur. The mutually engaging articulation surfaces of the femur and the patella together form, functionally, the patellofemoral joint, and the mutually engaging articulation surfaces of the femur and tibia together form, functionally, the tibiofemoral joint, which two functional joints together form the anatomical knee joint.

All or part of one or more of the articulation surfaces of the knee joint may fail to act properly, requiring the defective natural articulation surface to be replaced with a prosthetic articulation surface provided by an implantable prosthesis. To fit defects of varying scope, while allowing healthy portions of the knee joint to be conserved, a range of types of orthopedic knee implants is available. The range extends from total knee prosthesis systems for replacing the entire articulation surface of each of the femur, tibia and patella, to simpler systems for replacing only the tibiofemoral joint, or only one side (medial or lateral) of the tibiofemoral joint, or only the patellofemoral joint. Commonly employed orthopedic knee prostheses include components that fall within one of three principle categories: femoral components, tibial components, and patellar components. A so-called "total" knee prosthesis includes components from each of these categories. The femoral component replaces the distal end and condylar articulating surfaces of the femur and may include a proximal stem received within the medullary canal at the distal end of the femur. The tibial component replaces the proximal end and meniscal articulating surfaces of the tibia and may include a distal stem received within the medullary canal at the proximal end of the tibia. The patellar component replaces the posterior side and natural articulating surface of the patella. Sometimes, the patellar component is not used, and the natural articulating surface of the patella is allowed to articulate against the femoral component. A so-called "unicondylar" knee prosthesis replaces only the medial or the lateral femoral condylar articulating surface and the corresponding tibia[ meniscal articulating surface.

The acetabular cup component of a total hip prosthesis is configured to be received and fixed within the acetabulum of a pelvis. The pelvis is prepared to receive the acetabular cup by reaming a concavity in the acetabular bone. The acetabular cup component typically has an outer surface conforming to the concavity reamed in the acetabular bone of the pelvis, and an inner bearing cavity for receiving the head of the femoral component. The head articulates in the bearing cavity as a ball-and-socket joint to restore motion to a defective hip joint.

One known type of acetabular cup involves an acetabular shell made of a bio-compatible metal such as titanium or a titanium alloy, and a bearing insert made of a bio-compatible polymer such as ultra-high molecular weight polyethylene. The acetabular shell is shaped generally as a hemispherical cup having a dome, or apex, at a proximal end and an annular rim at a distal end. As used herein, the words proximal and distal are terms of reference that indicate a particular portion of a prosthesis component according to the relative disposition of the portion when the component is implanted. "Proximal" indicates that portion of a component nearest the torso, whereas "distal" indicates that portion of the component farthest from the torso. Between the dome and rim, the acetabular shell comprises a shell wall defined by a generally convex proximal surface and a generally concave distal surface spaced from the proximal surface. The concave distal surface defines a shell cavity having an opening at the rim of the cup for receiving the bearing insert. The bearing insert has a generally convex proximal surface configured to be received and fixed within the acetabular shell in generally congruent engagement with the concave distal surface of the shell wall. The bearing insert also has a bearing cavity that opens distally for receiving the head of the femoral component. The bearing cavity is defined by a generally spherical concave bearing surface having a radius similar to that of the femoral head component. The concave bearing surface articulates against the surface of the spherical femoral head component.

Acetabular shells of the type described can be affixed to the acetabular bone by bone screws or bone cement. If bone screws are elected, the screws are driven into the bone through the screw holes before the bearing insert is placed into the shell. The shell also can be affixed by a combination of bone screws and bone cement. The acetabular shell can be provided with more screw holes than typically would be used by the implanting physician. This provides a selection of sites for placement of the bone screws, as may be dictated by the condition of the patient's pelvic bone or by the physician's preference. Some provided screw holes may receive a screw while others do not. For reasons explained below, it is desirable to provide means for occluding those screw holes that will not receive a screw.

Commonly, acetabular shells of the type described also include a dome hole at the apex. A typical dome hole is coaxially aligned with the axis of symmetry of the acetabular shell and extends through the shell wall from the concave distal surface to the convex proximal surface of the acetabular shell. Often, the dome hole is internally threaded or otherwise configured for receiving an instrument for holding and positioning the acetabular shell during implantation. Also, many physicians use the dome hole to obtain visual or tactile access to the reamed acetabular bone during implantation of the acetabular shell. Such access allows the physician to confirm that the acetabular shell is fully seated in engagement with the reamed bony surface of the acetabulum. As with the screw holes, for reasons explained below, it is also desirable to provide means for occluding the dome hole.

The bearing insert is usually designed to be received within the acetabular shell in nonarticulating relative relationship. Nevertheless, a small amount of unintended relative motion is believed to occur between the bearing insert and the acetabular shell in response to the varying load borne by the acetabular cup during use. Such small relative motion, or micro-motion, may result in wear at the interface between the bearing insert and acetabular shell that generates fine polyethylene or metal debris. According to some hypotheses, such debris can migrate out of the acetabular cup and contact bone, possibly resulting in osteolysis, which ultimately can lead to bone resorption and possible loosening of the acetabular prosthesis. One apparent pathway for the migration of debris out of the acetabular shell is through open screw holes. Another apparent pathway is through an open dome hole.

The tibial component of a total knee prosthesis is configured to be received upon and fixed to the proximal end of the tibia. The tibia is prepared to receive the tibial component by resecting part of the proximal end of the tibia to leave a substantially horizontal planar bony plateau. Sometimes the exposed medullary canal at the proximal end of the tibia is also reamed to receive a stem portion of the tibial component. The tibial component typically includes a plate portion having an inferior planar surface conforming to the resected bony plateau at the proximal end of the femur. The plate portion may or may not include a depending stem or keel for receipt withing a prepared tibial medullary canal. Commonly, a meniscal bearing insert is received atop the plate portion of the tibial component to provide an artificial meniscal articulating surface for receiving the condylar surfaces of the femoral component of the total knee prosthesis. The femoral condylar articulating surfaces articulate against the tibial meniscal articulating surface to restore motion to a defective knee joint.

One known type of tibial component involves a tibial plate made of a biocompatible metal such as titanium or a titanium alloy, and a meniscal bearing insert made of a bio-compatible polymer such as ultra-high molecular weight polyethylene. The tibial plate is shaped generally as a flat plate having a perimeter that generally conforms to the transverse sectional perimeter of the resected proximal tibia. The tibial plate includes a planar distal, or inferior, surface for engaging the resected proximal tibia, and a proximal, or superior, surface for engaging and receiving the meniscal bearing insert. One or more screw holes may extend through the plate portion from the superior to the inferior surface. The bearing insert has an inferior surface that engages the superior surface of the plate portion, and may include locking tabs or other means for fixing the bearing insert to the plate portion against relative movement.

Tibial plates of the type described can be affixed to the resected tibial bone by bone screws or bone cement. If bone screws are elected, the screws are driven into the bone through the screw holes before the bearing insert is placed atop the plate portion. The plate also can be affixed by a combination of bone screws and bone cement. Sometimes the plate can be provided with more screw holes than typically would be used by the implanting physician. This provides a selection of sites for placement of the bone screws, as may be dictated by the condition of the patient's tibial bone or by the physician's preference. Some provided screw holes may receive a screw while others do not. For reasons similar to those discussed above regarding acetabular shells, and again briefly below, it is desirable to provide means for occluding those screw holes that will not receive a screw.

The tibial bearing insert usually is designed to be received atop the tibial plate in nonarticulating relative relationship.

Nevertheless, a small amount of unintended relative motion is believed to occur between the bearing insert and the tibial plate in response to the varying load borne by the tibial component during use. Such small relative motion, or micromotion, may result in wear at the interface between the bearing insert and acetabular shell that generates fine polyethylene or metal debris, similarly to the hypothesized phenomenon discussed above regarding acetabular shells. One apparent pathway for the migration of debris from the superior surface of the tibial plate is through open screw holes. In some total knee prostheses, the bearing insert is intended to articulate on the tibial plate in sliding or rotating relationship. Such knee prostheses are known as "mobile bearing" knees. The possibility of wear debris being generated in such knee prostheses is apparent.

SUMMARY OF THE INVENTION

According to one aspect of the present invention, an implantable orthopedic prosthesis includes a prosthetic component having a wall. The wall has a first surface for engaging bone and a second surface. The wall defines a hole therethrough extending from the second surface to the first surface. A plug is removably disposed in the hole and has a peripheral rim spring-biased radially outwardly in frictional engagement with the sidewall of the hole. It is an object of the present invention to provide an implantable orthopedic prosthesis, for engagement with bone, having one or more holes therethrough that can be selectively occluded with a plug to prevent migration of wear debris therethrough.

Other objects and advantages of the present invention will be apparent from the following descriptions of the preferred embodiments illustrated in the drawings.

DESCRIPTION OF THE PREFERRED EMBODIMENTS

Figure 1:
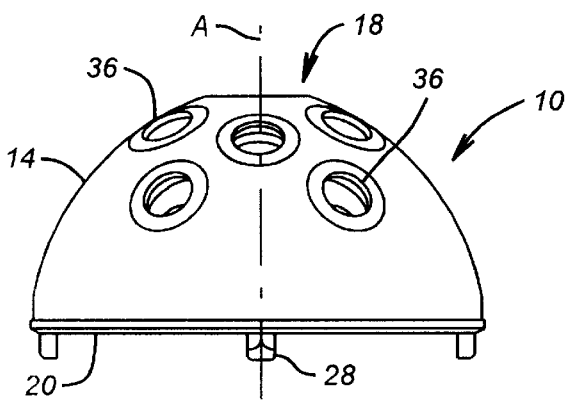
FIG. 1 is an elevation view of an acetabular shell constructed according to the present invention.

Referring to the drawings, FIGS. 1–5, a preferred embodiment of the present invention is illustrated as an implantable orthopedic prosthesis, particularly an acetabular shell component of a total hip joint prosthesis. The illustrated acetabular shell is useful as one component of that well-known type of total hip joint prosthesis that includes an acetabular shell and an associated bearing liner, and a femoral stem and an associated spherical head. The spherical head, fixed to the femoral stem, articulates in a ball-and-socket arrangement within the bearing liner, with the bearing liner being essentially fixed within the acetabular shell. The femoral stem and acetabular shell are fixed to bone of the proximal femur and pelvic acetabulum, respectively. Only the acetabular shell is described in detail herein, as the various types and forms of bearing liners and the means for affixing such bearing liners within an acetabular shell are well understood in the art. The illustrated acetabular shell is particularly advantageous for preventing potentially osteolytic polyethylene particles from migrating out of the acetabular shell, when used with a bearing liner made of ultra-high molecular weight polyethylene. The utility of the invention is not limited to the use of any particular bearing liner material, however.

Figure 2:
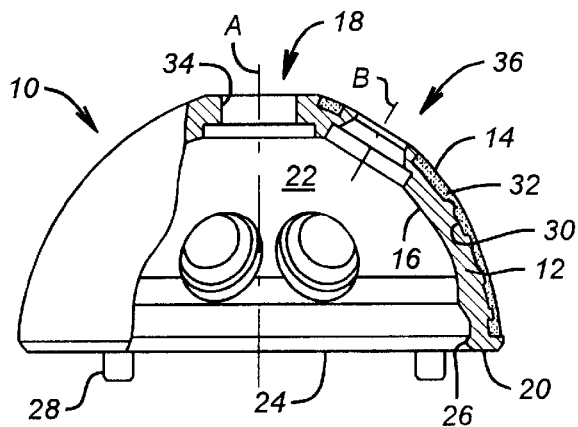
FIG. 2 is a partial sectional view of the acetabular shell of FIG. 1, taken in the plane of the axis A of the acetabular shell.

Referring to FIGS. 1 and 2, an acetabular shell 10 is shaped generally as a hemispherical cup having a shell wall 12 defined by a convex proximal surface 14 and a concave distal surface 16. Acetabular shell 10 has a proximal dome region 18 at the apex of shell wall 12 and an annular rim 20 at the distal end of shell wall 12. Shell wall 12 is generally symmetrical about an axis A that passes through the center of proximal dome region 18 at the apex of shell wall 12. Concave distal surface 16 of shell wall 12 defines a shell cavity 22 having an opening 24 into and through which a bearing insert (not shown) can be received. The preferred bearing insert is made of ultra high molecular weight polyethylene and has a partially spherical bearing cavity that opens distally for receiving a spherical head of a femoral component (not shown) in a ball-and-socket articulating relationship. An annular lip 26 extending radially inwardly from concave distal surface. 16, in cooperation with an annular protrusion on the bearing insert, provides a means for affixing the bearing insert against axial displacement within shell cavity 22. An annular flange on the bearing insert has notches for receiving the legs 28 that extend axially from rim 20. The engagement of the legs 28 and the notches of the bearing insert flange provides a means for affixing the bearing insert against rotation within shell cavity 22. Convex proximal surface 14 is provided with a macro-texture comprising circumferential grooves 30 filled and covered with a porous coating 32 comprising sintered titanium particles. The porous coating 32 accepts the ingrowth or ongrowth of bone, and enhances adhesion of bone cement. The porous coating 32, while preferred, is not necessary for the understanding or practice of the present invention.

Referring again to FIG. 2, acetabular shell 10 includes a dome hole 34 centered at the apex of dome region 18 in coaxial alignment with axis A. Dome hole 34 is internally threaded to serve as an engagement interface for an instrument (not shown) for holding and positioning acetabular shell 10. Typically, such an instrument is used by the implanting physician to securely grasp the acetabular shell and place it in the reamed acetabulum. Such an instrument usually includes an elongate handle for controlling anteversion and adduction of the acetabular shell as it is implanted, and for transmitting axial driving forces to the shell.

Figure 3:
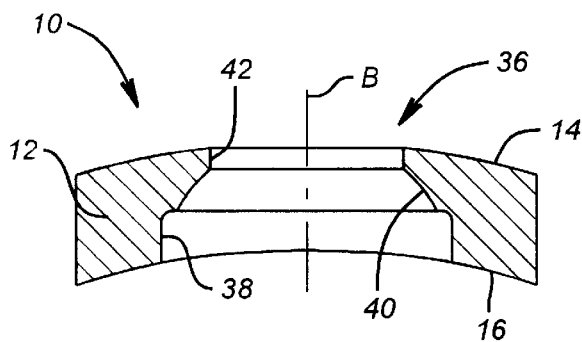
FIG. 3 is a detail sectional view of a screw hole of the acetabular shell of FIG. 1 taken in a plane that includes the central axis B of the screw hole.

Referring to FIG. 3, and to FIGS. 1 and 2, acetabular shell 10 is provided with a plurality of screw holes 36 disposed through shell wall 12 in various locations. The screw holes 36 are provided in superabundance compared with the number of bone screws usually employed to implant the acetabular shell 10. Therefore, the physician is presented with a selection of variously placed screw holes from which to choose. Those screw holes 36 that are not selected by the physician to receive a bone screw will be occluded during the implanting procedure, according to the present invention. Occlusion of unused screw holes 36 is desirable to alleviate the risk of polyethylene debris migrating from shell cavity 22 through open screw holes 36. Such polyethylene debris, according to a prevailing hypothesis, can be generated by frictional wear caused by micro-motion between the acetabular shell and its polyethylene bearing liner. By design, the polyethylene liner is intended to fit congruently against concave distal surface 16, without any articulation against the acetabular shell 10. Nevertheless, according to the hypothesis, some relative micro-motion inevitably occurs. The reason for concern over such polyethylene wear debris is that in vitro experiments have shown that fine polyethylene particles are osteolytic.

Each screw hole 36, beginning at concave distal surface 16 and progressing through shell wall 12 to convex proximal surface 14, includes a substantially cylindrical first portion 38, followed by a concave spherical second portion 40, followed finally by another substantially cylindrical third portion 42. Screw holes 36 are designed to receive a well-known bone screw (not shown) that includes a head and a threaded shank. The undersurface of the head, i.e., that portion of the head adjacent the shank, is convexly spherically shaped, with substantially the same radius of curvature as that of spherical second portion 40 of screw hole 36. This allows congruent contact to be maintained between the undersurface of the bone screw and spherical second portion 40 of screw hole 36 despite angular misalignment of the shank relative to the axis B of screw hole 36. As an alternative, second portion 40 of screw hole 36 can be configured as a truncated cone. Such a conical second portion can receive bone screws having heads with either spherical or conical undersurfaces. Using a bone screw having a conical undersurface with a screw hole having a conical second portion results in loss of the benefit of maintaining congruent contact despite misalignment.

Figure 4:
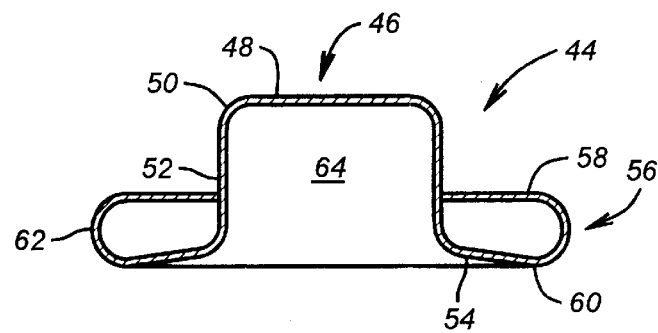
FIG. 4 is a sectional view of a screw hole plug constructed according to the present invention and useful in combination with the acetabular shell of FIG. 1.

Referring to FIG. 4, a screw hole plug 44 is shown that is useful in combination with the acetabular shell 10 described above. More particularly, screw hole plug 44 is useful for occluding any unused screw hole 36 to alleviate the risk of polyethylene debris migrating from shell cavity 12 through any such unused screw holes. Screw hole plug 44 is made of titanium or titanium alloy sheet metal and is formed by stamping the sheet metal between a mating punch and die, according to well-known metal fabrication techniques. The sheet metal from which screw hole plug 44 is formed is preferred to have a thickness of about 0.005 inches, but may range from about 0.002 inches to about 0.010 inches in thickness. After stamping, and rolling of the peripheral edge, according to well-known machine tool operations, the resulting screw hole plug 44 includes a crown 46 having a generally flat top wall 48 connected through a radiused annular perimetrical edge 50 to a generally cylindrical side wall 52. Crown 46 has an outside diameter at side wall 52 that is less than the inside diameter of third cylindrical portion 42 of screw hole 36. Descending from side wall 52 of crown 46 is an annular, frusto-conical skirt 54 extending radially outwardly and distally. Skirt 54 terminates in an annular, partially-rolled peripheral rim 56 having a free edge 58 that extends proximally from the distal extent 60 of peripheral rim 56 and extends radially inwardly from the radial extent 62 of peripheral rim 56. In cross-section, peripheral rim 56 is generally semicircular. Skirt 54 and partially-rolled peripheral rim 56, as configured, render screw hole plug 36 sufficiently flexible, yet springy, to allow a slight radial, elastic compression of the radial extent 62 of peripheral rim 56 in response to the application of appropriately directed forces, the significance of which is explained further below.

Figure 5:
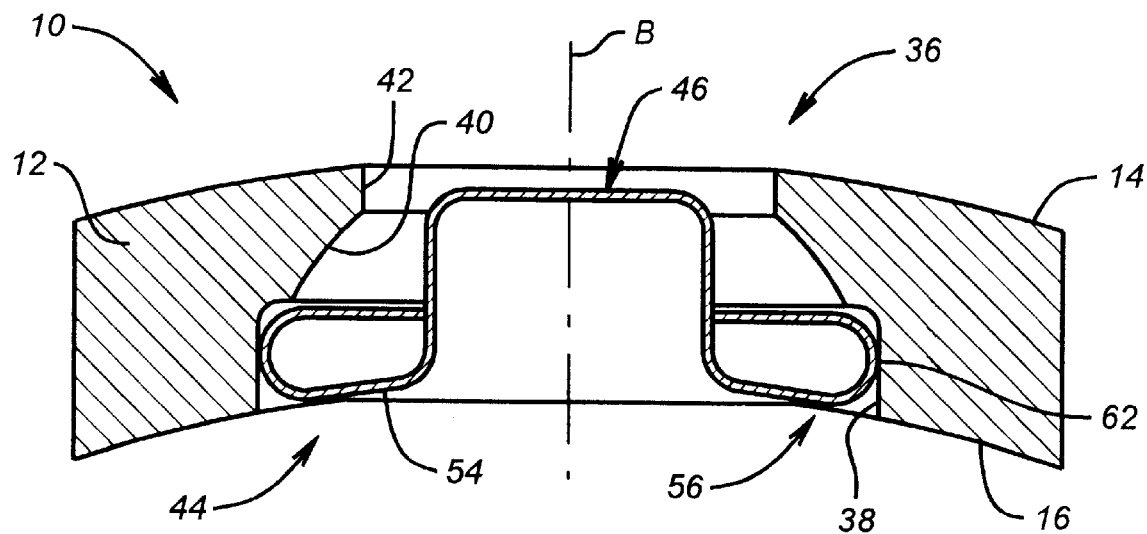
FIG. 5 is a detail sectional view of the screw hole of the acetabular shell of FIG. 1 taken in a plane that includes the central axis B of the screw hole, in which is received the screw hole plug of FIG. 4, which plug is also shown in section in the same plane.

Referring especially to FIGS. 4 and 5, the operation and advantages of screw hole plug 44 are made clear. Screw hole plug 44 has been placed within a selected screw hole 36 of acetabular shell 10, having been inserted from the end of screw hole 36 adjacent concave distal surface 16. Crown 46 is disposed, in non-engaging fashion, within the interior of screw hole 36 defined by second spherical portion 40 and third cylindrical portion 42. Peripheral rim 56 is disposed in spring-loaded engagement with first cylindrical portion 38 of screw hole 36. As manufactured, screw hole plug 44 has a natural, or unloaded, outside diameter at the peripheral extent 62 that is slightly greater than the inside diameter of first cylindrical portion 38. The preferred diametrical oversize is about 0.005 inch, which results in a tangential, spring-loaded press fit between the peripheral extent 62 of rolled peripheral rim 56 and first cylindrical portion 38 of screw hole 36. Radially outwardly directed forces, generated by the spring action of screw hole plug 44, establish a continuing frictional engagement between peripheral extent 62 and first cylindrical portion 38. Radially inward compression of peripheral extent 62 is aided, upon insertion of screw hole plug 44 into screw hole 36, by a slight distal deflection of skirt 54 relative to crown 46 occasioned by friction between peripheral extent 62 and first cylindrical portion 38. This friction opposes movement of screw hole plug 44 in the proximal direction during insertion. As preferred, insertion is accomplished with an instrument (not shown) received within the interior cavity 64 of screw hole plug 44 in engagement with the interior surface of top wall 48 and moved proximally relative to acetabular shell 10 in alignment with the axis B of screw hole 36.

Figure 6:
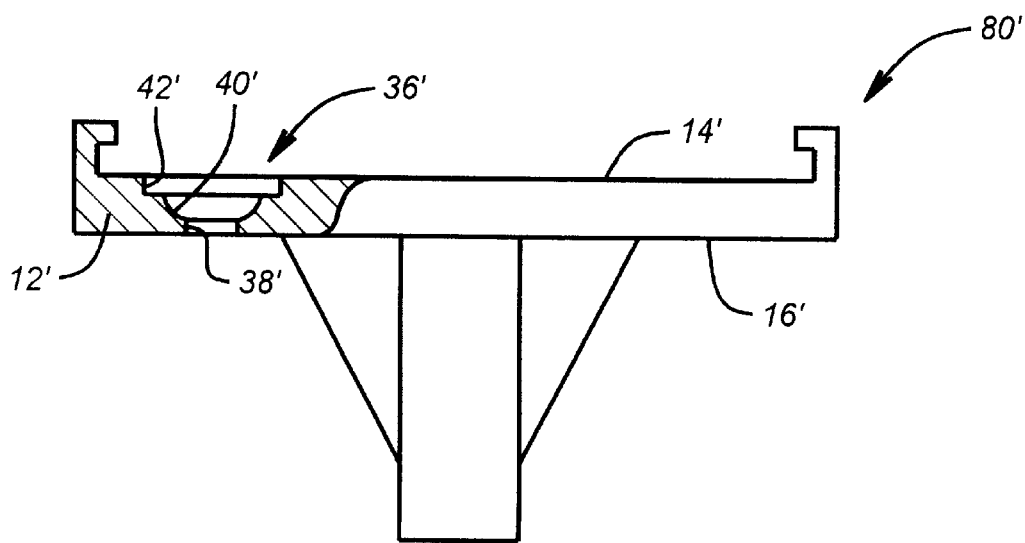
FIG. 6 is an elevation view, partially in section, showing a tibial component constructed according to the present invention, comprising a second embodiment of the invention.

Referring to FIG. 6, there is illustrated, in partial cross-section, a second embodiment of the present invention as a tibial baseplate component 80 of an implantable total knee prosthesis. Plate 80 includes a screw hole 36, that is substantially similar to the screw hole 36 described above for an acetabular shell, for receiving the above described screw hole plug 44. Other portions of the above-described screw hole 36 are indicated by like primed reference numerals. The second embodiment of FIG. 6 differs from the first described embodiment of FIGS. 1–5 principally in that the wall 12, through which screw hole 36' extends is planar, rather than hemispherical. In other pertinent respects, the above description of the first embodiment applies as well to the second embodiment of FIG. 6.

The present invention has been illustrated and described with particularity in terms of preferred embodiments. Nevertheless, it should be understood that no limitation of the scope of the invention is intended. The scope of the invention is defined by the claims appended hereto. It should also be understood that variations of the particular embodiments described herein incorporating the principles of the present invention will occur to those of ordinary skill in the art and yet be within the scope of the appended claims.

What is claimed is:

1. An implantable orthopedic prosthesis comprising:
   a prosthetic component having a wall, said wall having a first surface for engaging bone and having a second surface, said wall defining a hole extending from said second surface to said first surface, said hole being defined by a sidewall; and
   a plug removably disposed within said hole, said plug including a crown portion at a proximal end and a rolled flexible skirt at a distal end, said skirt extends outwardly from and circumferentially around said crown portion, said skirt deflecting distally relative to the crown portion in response to a biasing against said rim when said plug is positioned in said sidewall of the hole.

2. The implantable orthopedic prosthesis according to claim 1, wherein said skirt has a frusto-conical shape and extends radially outwardly from said crown.

3. The implantable orthopedic prosthesis according to claim 1, wherein said peripheral rim has a circular configuration.

4. The implantable orthopedic prosthesis according to claim 3, wherein said circular configurations bends upwardly away from said skirt.

5. The implantable orthopedic prosthesis according to claim 3, wherein said plug further includes a flat portion that extends from said circular configuration and terminates adjacent said crown.

6. The implantable orthopedic prosthesis according to claim 5, wherein said flat portion is positioned above said skirt.

7. The implantable orthopedic prosthesis of claim 1, wherein said crown includes a top wall and a substantially cylindrical sidewall.

8. The implantable orthopedic prosthesis of claim 7, wherein said skirt extends outwardly from a distal end of said sidewall of said crown.

9. The implantable orthopedic prosthesis of claim 7, wherein said top wall of said crown, said sidewall of said crown, and said skirt are integrally formed together.

10. The implantable orthopedic prosthesis of claim 7, wherein said top wall of said crown, said sidewall of said crown, and said skirt have a substantially uniform thickness.

11. An implantable orthopedic prosthesis, comprising:

an acetabular shell having a substantially concave inner surface defining a cavity;

a plurality of holes disposed through said shell, said holes having a diameter extending between a circular sidewall in said shell; and a plurality of plugs for sealing said holes, wherein each of said plugs includes a crown having a dome configuration with a top portion and a sidewall extending downwardly from said top portion, a skirt integral with said crown and extending radially outwardly from said crown, a peripheral rim integral with said skirt and having an outer diameter that is larger than said diameter of said hole, and wherein said rim extends back toward said crown and terminates at said sidewall and deflects radially inwardly when said rim engages with and is biased against said sidewall of said hole.

12. The implantable orthopedic prosthesis of claim 11, wherein:

said skirt extends outwardly from said crown and terminates at said rim; and said rim has a semi-circular configuration that bends upwardly away from said skirt.

* * * * *